United States Patent [19]

Fuerthbauer et al.

[11] Patent Number: 4,920,257

[45] Date of Patent: Apr. 24, 1990

[54] LIGHT FILTER WITH AUTOMATIC REGULATION OF OPTICAL TRANSMISSION

[76] Inventors: Rupert Fuerthbauer; Rolf Bruhin, both of Kratzstrasse 35, CH-8620 Wetzikon, Switzerland

[21] Appl. No.: 107,331

[22] Filed: Oct. 9, 1987

[30] Foreign Application Priority Data

Oct. 9, 1986 [DE] Fed. Rep. of Germany ....... 3634508

[51] Int. Cl.$^5$ .......................... G02F 1/13; G05D 25/02
[52] U.S. Cl. .................................. 250/201.1; 250/205; 350/332; 350/356
[58] Field of Search ................ 250/201, 205; 350/356, 350/332, 384

[56] References Cited

U.S. PATENT DOCUMENTS

| | | | |
|---|---|---|---|
| 3,962,576 | 6/1976 | Kuhl et al. .......................... | 250/201 |
| 4,071,751 | 1/1978 | Waksberg ........................... | 250/201 |
| 4,162,398 | 7/1979 | Kayanuma ........................... | 250/205 |
| 4,378,490 | 3/1983 | d'Auria Luigi ..................... | 250/205 |

FOREIGN PATENT DOCUMENTS 2442998 8/1976 Fed. Rep. of Germany .

Primary Examiner—Edward P. Westin
Attorney, Agent, or Firm—Tarolli, Sundheim & Covell

[57] ABSTRACT

The invention relates to improvement in a light filter with automatic regulation of the optical transmission. The filter comprises a filter element (1) with a liquid crystal layer located between two transparent plates (2) and assigned polarizers. The optical transmission of the light filter is varied by applying a variable electric voltage. A first optical sensor (4) is arranged behind the filter element (1) in the radiation emitting direction, and a second optical sensor (8) is arranged beside or in front of the filter element (1) in the radiation emitting direction. The two sensors are connected to a regulating circuit (6), which comprises a subtraction circuit (15) which subtracts the signal generated by the second optical sensor (8) from the signal of the first optical sensor (4), or the signal of the first optical sensor (4) from the signal of the second optical sensor (8), so that the output signal of the regulating circuit is at least approximately proportional to the amount of visible light. As the second optical sensor (8) a sensor sensitive only to infrared radiation, may be used or, if this is also sensitive to other radiation, an infrared band-pass filter may be placed in front of it.

15 Claims, 2 Drawing Sheets

LIGHT FILTER WITH AUTOMATIC REGULATION OF OPTICAL TRANSMISSION

The present invention relates to a light filter having automatic regulation of the optical transmission.

The filter has a filter element which is adjustable to vary its optical transmission of visible light. An optical sensor detects incident and/or background light transmitted through the filter and is connected to a regulating circuit. The circuit produces an electric signal necessary for the regulation of the optical transmission of the filter element dependent on the radiation falling on the sensor. The sensor is arranged behind the filter element in the radiation emitting direction.

The invention also contemplates a light filter with automatic regulation of the optical transmission which has two filter elements adjustable in relation to their optical trasmission of visible light, and an optical sensor which detects the incident and/or background light and is connected to a regulating circuit which produces the electric signal needed for the regulation of the optical transmission of the filter element dependent on the radiation falling on the sensor.

Such light filters are used, for example, as protective filters in the protective shields or helmets, etc., of welders, in order to protect the person operating the welding apparatus from the extremely bright radiation occurring during welding. On the other hand, other uses are also possible, for example, in sunglasses, window panes for buildings, auto or aircraft windows etc.

A sighting window with automatic regulation of light transmission is known from German Laid-Open Patent Application No. 2,442,998 among others. There, a so-called liquid crystal cell, that is, a liquid crystal element is used for light screening. The amount of light behind the sight window is measured by a photosensor and a signal is fed as a regulating variable to a control circuit which adjusts the control voltage for the crystal layer so that the amount of light allowed to pass through corresponds to a preselected desired value.

Theoretically, such an arrangement may function, but it has been found that the occurrence of infrared radiation can sensitively disturb this regulating mechanism. But since, in welding applications, increasingly and almost always, a strong infrared radiation occurs, the device proposed in the above-mentiond German disclosure has only limited use for welder's protective shields or helmets. There is limited use since strong sunshine, but especially the work of a nearby fellow welder, can badly impair the regulation, because of a strong infrared radiation which can unexpectedly blank the protective shield or helmet.

Invisible ultraviolet radiation, also present, affects little or not at all an arrangement with a first sensor placed behind a liquid crystal cell. This occurs because liquid-crystal cells, as we know, let through infrared radiation almost unhindered, but largely screen out the ultraviolet radiation, especially when provided, as usual, with polarizers in front of and behind them. Moreover, usual photosensors, besides their sensitivity in the visible range of the spectrum, have little or no sensitivity to ultraviolet radiation, but are very sensitive to infrared radiation.

The object of the present invention is to improve a light filter of the kind mentioned so that in its regulating behavior, it responds mainly to visible light but hardly at all to infrared radiation. The latter is much less harmful to persons.

According to the first embodiment of the invention, this object is achieved in a light filter of the kind first mentioned by providing a second sensor in an arrangement with a single light filter element which is adjustable in its optical transmission. The second sensor is arranged beside or in front of the filter element, in the direction of radiation emission. A subtraction circuit that forms part of the regulating circuit is provided. The subtraction circuit subtracts the signal generated by the second sensor from the signal of the first optical sensor, or the signal of the first optical sensor from the signal of the second sensor, so that the output signal of the regulating circuit is at least approximately proportional to the amount of visible light in front of the filter element.

In an arrangement with two light filter elements, switched on in series and adjustable in their optical trasmission, the object of the invention is achieved according to claim 2, by arranging a first optical sensor functionally behind the first filter element in the direction of radiation emission and by providing a second sensor which is arranged beside or in front of the first filter element in the radiation emission direction, and by providing a subtraction circuit in the regulating cicuit which subtracts the signal generated by the second sensor from the signal of the first optical sensor, or the signal of the first optical sensor from the signal of the second sensor, so that the output signal of the regulating circuit is at least approximately proportional to the amount of visible light in front of the filter element.

In each case, therefore, it is assured that, through the subtraction, the influence of infrared radiation is eliminated and that the regulating circuit functioning depends only on the amount of visible light. As it has already been mentioned, ultraviolet radiation has only a slight influence, and can be further reduced, if desired, by arranging an ultraviolet blocking filter in front of one or both of the sensors.

With a view to simplicity of construction, it may be advantageous if the first optical sensor and the second sensor are identical. This provides a further advantage of their sensitivity being the same. This reduces expenses for the regulating circuit and improves regulation. With this arrangement a negative or positive control signal is obtained according to the kind of circuit. The signal corresponds to the difference between the light actually present and the filtered visible light, that is, to the amount of visible light behind the light filter element without the infrared component.

Another solution may consist in that the first sensor arranged behind the light filter element is sensitive to infrared radiation and visible light, but the second sensor is sensitive only to infrared radiation. After subtraction, according to the circuit, a positive or negative signal is obtained, which is directly proportional to the visible light component without infrared radiation. The disadvantage here is that two different sensors, possibly with different sensitivity, or sensors with different characteristics, must be used. This can be compensated, however, by arranging an adjustable amplifier after one or both sensors. The advantage of the first mentioned regulating circuit is that it is simpler.

Other embodiments and further features of the subject invention are defined in the dependent claims.

The invention will be explained in detail below, with reference to the attached drawings, which show schematically several embodiments:

Figure 1:
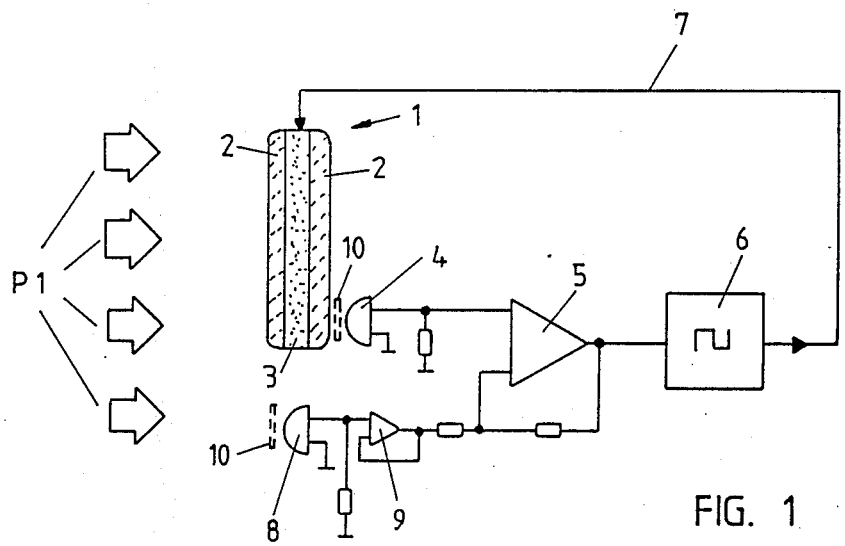
FIG. 1 shows a first embodiment with a single filter element.

According to FIG. 1, the light filter according to the invention includes, for example, a liquid crystal cell 1; that is, a liquid crystal element consisting, in principle, of two parallel glass panes 2 with a liquid crystal layer 3 between them. The glass panes may themselves act as polarizers, or separate polarizers may be provided for the liquid crystal elements. Such elements are known and are characterized by the fact that such a filter element, by applying a variable alternating voltage to the liquid crystal layer 3, can be changed from a substantially transparent condition to a substantially opaque condition.

Behind the liquid crystal cell 1 is arranged a first photosensor 4 which picks up the radiation let through by the cell 1, and generates an output signal proportional to the received intensity of the radiation. A differential amplifier 5, which will be discussed later, transmits the output signal of the first sensor 4 to a regulating circuit 6, which processes the signal and, in turn, generates an output control signal directed through a line 7 to the liquid crystal cell 1. The arrangement is such that the cell 1 is blanked when the first sensor 4 receives much light, and vice versa; such a device is known and need not be explained here.

The arrangement shown in FIG. 1 includes also a second sensor 8, which in the present case is arranged beside the cell 1. It might equally well be arranged in front of the cell 1 since it is only essential that it always receives the total amount of existing radiation without being influenced by the cell 1. The second sensor 8 generates an output signal dependent on the received radiation and which is transmitted to an impedance transformer 9 the output of which is connected to the second input of the differential amplifier 5. Ultraviolet blocking filters might be installed in front of the sensor 4 and/or the sensor 8 to filter out any disturbing ultraviolet radiation.

The circuit functions as follows:

Radiation, from a welding spot, for example, and thus containing a (relatively strong) infrared component, a visible light component and, possibly, an ultraviolet component, also is emitted in the direction P1 as shown by arrows. The cell 1 is in an open condition, and the sensor 4 receives almost all the radiation. In any case, it should be noted that a liquid crystal cell, even in an open condition, already acts as an ultraviolet blocking filter, so that, practically, at first, the total amount of infrared radiation and visible light is received by the sensor 4. The regulating circuit 6 is designed in the known way, so that it delivers at once an output signal to the cell 1, which acts within milliseconds, so that the cell 1 is blanked; that is, its radiation permeability is reduced. A control circuit, which may be provided, permits to set the regulating circuit 6 to a certain preselected blanked value.

The distinction of such an arrangement, however, is that, even with the occurrence of infrared radiation alone, or with a strong component of radiation of such wavelengths, a response of the regulating circuit and, thus, blanking of visible light takes place. However, in many cases, this is highly undesirable; for example, in case of a strong sunlight or with an infrared radiation caused by a neighboring workplace.

Providing a remedy here is the object of the present invention. This takes place, in the first discussed embodiment and shown schematically in FIG. 1, in the following way:

Let us assume that the two sensors namely sensors 4 and 8, are identical; that is, equally sensitive to infrared radiation and to visible light. The sensor 4 receives all, or practically all infrared radiation and a component of visible light when the liquid crystal cell is blanked. The sensor 8, on the other hand, receives all the infrared radiation as well as all the radiation in the visible range of the spectrum, since, according to the invention, it is placed in front of or beside the liquid crystal cell 1. The ultraviolet radiation component is practically negligible.

Let:

IR = IR radiation component $S_v$ = component of visible radiation behind the liquid crystal cell $S_k$ = component of visible radiation in front of the liquid crystal cell $A_{o1}$ = proportionality factor of the output signal of the subtraction circuit.

Then, according to whether the sensor 4 is connected to the noninverting inlet, and the sensor 8 to the inverting inlet of the differential amplifier 5, or conversely:

$$(S_v + IR) - (S_k + IR) = S_v - S_k = -A_{o1}'$$

or $$-(S_v + IR) + (S_k + IR) = -S_v + S_k = +A_{o1}'$$

In both cases, therefore, a factor is obtained, independent of the infrared component, which is used to control the liquid crystal cell 1 and which is also influenced by the visible light component behind the cell 1, so that it can be used as a regulating variable.

The arrangement discussed above has the advantage that two identical sensors (4 and 8) can be used, of which the characteristics may also be equal or very similar; however, the costs of evaluating the output signal, $A_{o1}$ or $-A_{o1}'$, is somewhat greater.

In order to avoid these costs, it is possible to use two different sensors 4 and 8. The sensor 4, after the cell 1, is sensitive to infrared radiation and to visible light; the sensor 8, beside or in front of the cell 1, on the other hand, is sensitive only to infrared radiation. Then, based on the above definitions, dependent, again, on how the two sensors are connected to the differential amplifiers:

$$(S_v + IR) - IR = S_v = A_{o2}'$$

or $$-(S_v + IR) + (IR) = -S_v = -A_{o2}'$$

Here again, the output signals $A_{o2}$ or $-A_{o2}'$, are free of any infrared component and also directly proportional to the amount of visible light received behind the cell 1. Thus, they may be processed simply and directly, in the regulating circuit.

Figure 2:
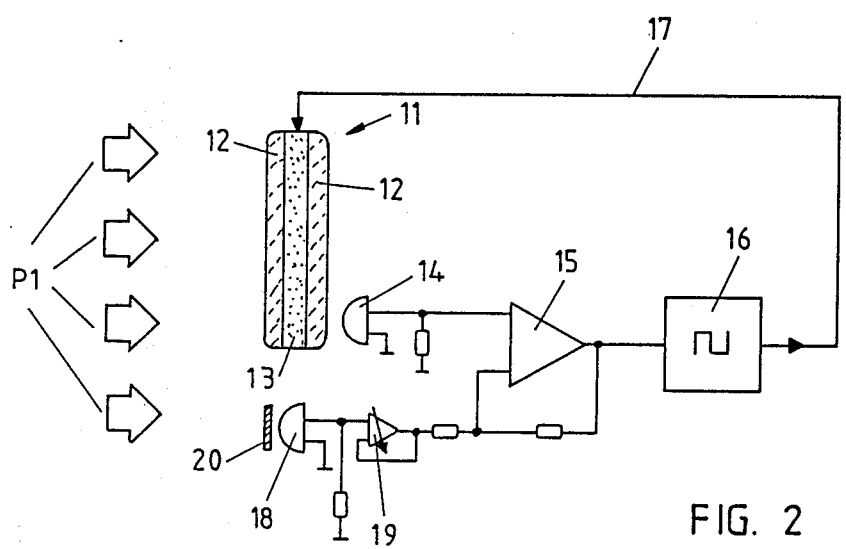
FIG. 2 shows a modified form of the first embodiment.

With this arrangement, two different sensors might be used as sensors 4 and 8, or, as in FIG. 2, identical sensors 14 and 18 might be used, with an infrared band-pass filter being placed in front of the sensor 18. The rest of the arrangement, with a liquid crystal cell 11, consisting of two parallel glass plates 12, a liquid crystal layer 13 lying between them, possible separate polarizers (not shown), a photosensor 14 arranged behind a differential amplifier 15, a regulating circuit 16, connected through a line 17 with the cell 11, and an impedance transformer/amplifier 19, is, in principle, exactly the same. However, it may be recommended here that the electric circuit 19 be adjustable in its gain to be able to compensate any losses of sensitivity caused by the filter 20.

Figure 3:
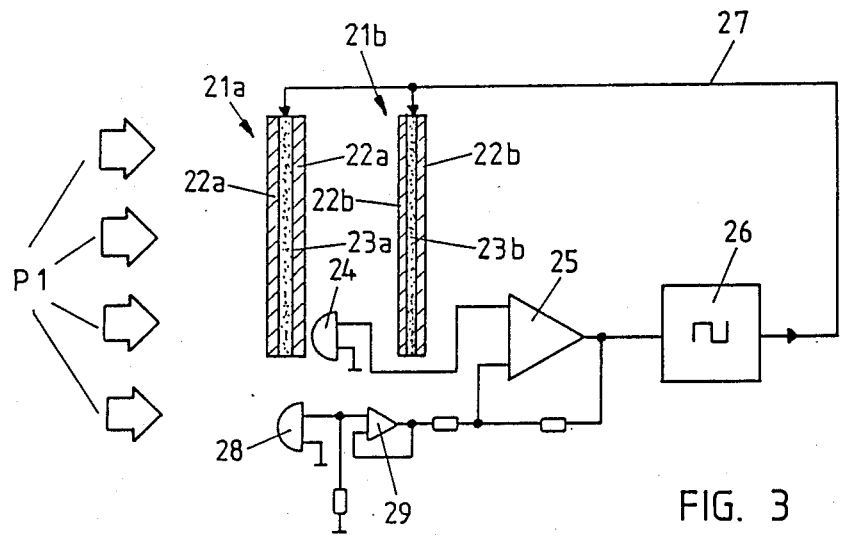
FIG. 3 shows a second embodiment with two filter elements connected one after the other.

In FIG. 3 is shown a second embodiment of the invention. Unlike the design in FIGS. 1 and 2, two liquid crystal cells 21a and 21b, connected one after the other, are used here, in order to obtain a stronger damping of light which is sometimes desirable. For the rest, these structures are the same, with a liquid crystal layer 23a or 23b, between two parallel glass plates 22a or 22b, in each case, which themselves act as polarizers, or with separate polarizers (not shown) located in front of and behind the cells. The first photosensor 24 is arranged after the first cell 21a but in front of the cell 21b, in the radiation emitting direction P1, so that a sufficient residual amount of light falls on the sensor, which is necessary for actuation of the regulating circuit 26.

Correspondingly, a second sensor 28 is arranged beside or in front of the first cell 21a, which, as it was already mentioned, receives either the whole radiation spectrum or only the infrared component, and conducts its output signal through a possibly adjustable impedance transformer-amplifier 29 to a differential amplifier 25. The output of the regulating circuit 26 is conducted through a line 27 to the two cells 21a and 21b, connected one after the other, while means (not shown) may possibly be provided for the opposite-phase actuation of the cells.

As to the spectrum sensitivity of the cells 24 and 28, or the filters (not shown), arranged in front of them in all cases, what has been said above applies in principle.

Figure 4:
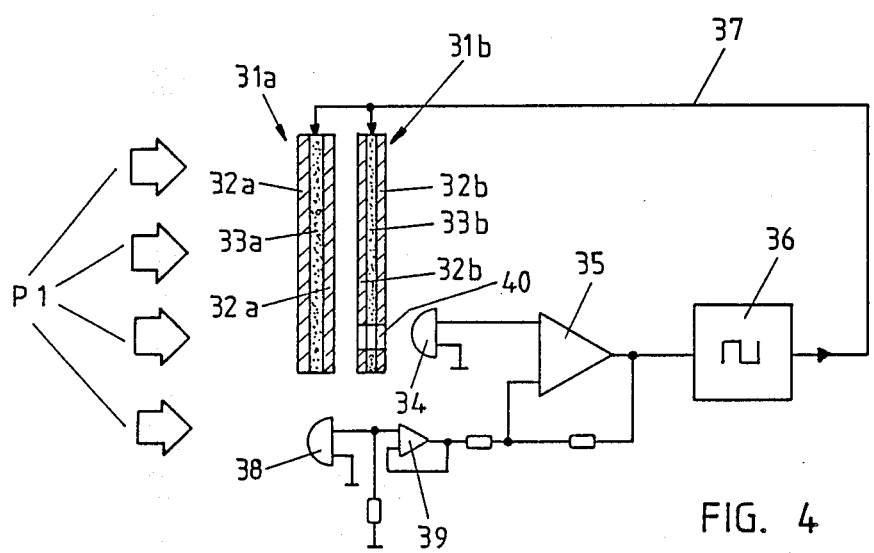
FIG. 4 shows a modified form of the second embodiment.

If, for physical reasons or from commercial considerations, it is impossible to place the sensor 24 between the cells 21a and 21b, a solution according to FIG. 4 may be considered. Here, two liquid crystal cells 31a and 31b, arranged more closely to each other and arranged one behind the other in the light-emitting direction P1, are provided. Each cell consists of two parallel glass plates 32a and 32b and a liquid crystal layer 33a or 33b between them. As to polarizers, what has been said before applies.

The first photosensor 34 can be mounted behind the first cell 31a, but can be arranged, physically, after the second cell. The second cell 31b is provided with an opening 40, which always remains open so that no changes in optical transmission behavior occur even when the cell 31b is blanked. This is advantageous whenever the two liquid crystal cells 31a and 31b, unlike the schematic representation in the drawing, are very narrow or must be placed very close to each other. The small opening 40 at the edge of the cell 31b hardly disturbs the behavior and effect of the total arrangement, or not at all. For the rest, the structure of the arrangement, with a second sensor 38, the impedance transformer-amplifier 39, the differential amplifier 35, and the regulating circuit 36, connected to the cells 31a and 31b through the line 37, are the same as described before.

Naturally, in the arrangement according to FIG. 3 and FIG. 4, respectively, the sensors 24 and 34, on the one hand, and 28 and 38, on the other hand, are of the same type, possibly with band-pass filter (not shown) before the sensor 28 or 38. Alternatively, different types may be used; that is, sensor 24 or 34 may be sensitive to infrared and to visible light, and sensor 28 or 38, on the other hand, may be sensitive only to infrared component. What has been said before as to the adjustable gain of the impedance transformer-amplifier 25 or 35, also applies in principle.

Finally, it should be mentioned that polarization filters must be located in front of and behind the liquid crystal cells, for example, as known in the state of the art, for example, from U.S. Pat. No. 4,039,354.

It is important according to the invention that the influence of infrared radiation on the regulating circuit be eliminated, and that an infrared blocking filter be electrically simulated. In this way, an effective, reliable regulation of the light permeability of the light filter, whether it consists of one cell or of two cells located one behind the other, is always assured, even when strong infrared radiation prevails in the background, since the regulating circuit now responds only to visible light. The ultraviolet radiation, also present, hardly interferes, since most photosensors, as already mentioned, hardly respond to this, and since a liquid crystal cell is in itself already a good ultraviolet blocking filter.

We claim:

1. Light filter means with automatic regulation of optical transmission comprising:
   a liquid crystal filter element which is adjustable to vary the optical transmission of visible light therethrough;
   a first optical sensor for detecting incident and background light, said first optical sensor producing an electric signal for regulating the optical transmission of said liquid crystal filter element in accordance with the radiation received by said first sensor, said first optical sensor being located behind said liquid crystal filter element in the direction of radiation emission;
   a second optical sensor being arranged beside or in front of said liquid crystal filter element in the radiation emitting direction;
   a regulating circuit for controlling the optical transmission of visible light through said liquid crystal filter element including a subtraction circuit which subtracts the signal generated by one of said first and second optical sensors from the signal of the other of said first and second optical sensors, the output signal of said regulating circuit being at least approximately proportional to the amount of visible light in front of said filter element.

2. Light filter means according to claim 1 wherein said first optical sensor and said second optical sensor have substantially the same sensitivity characteristics.

3. Light filter means according to claim 2 wherein said first optical sensor and said second optical sensor are sensitive to infrared radiation and to visible light.

4. Light filter means according to claim 2 wherein at least one of said first and second optical sensors is connected through an amplifier to said subtraction circuit of said regulating circuit.

5. Light filter means according to claim 2 wherein at least one of said first and second optical sensors is connected through an impedance transformer to said subtraction circuit of said regulating circuit.

6. Light filter means according to claim 2 further including a neutral density filter for visible light arranged in front of at least one of said first and second optical sensors.

7. Light filter means according to claim 2 wherein said subtraction circuit includes a differential amplifier, said first optical sensor being connected to the noninverting input thereof and said second optical sensor being connected to the inverting input thereof so that a negative signal is fed to said regulating circuit, the negative signal being proportional to the visible light component and being independent of the infrared radiation.

8. Light filter means according to claim 2 wherein said subtraction circuit includes a differential amplifier, said first optical sensor being connected to the inverting input thereof and said second optical sensor being connected to the noninverting input thereof so that a positive signal is fed to said regulating circuit, the positive signal being proportional to the visible light component and being independent of the infrared radiation.

9. Light filter means according to claim 1 wherein said first optical sensor is sensitive to infrared radiation and visible light and said second optical sensor is sensitive only to infrared radiation.

10. Light filter means according to claim 9 wherein said subtraction circuit includes a differential amplifier, said first optical sensor being connected to the noninverting input thereof and said second optical sensor being connected to the inverting input thereof so that a negative signal is fed to the regulating circuit, the negative signal being proportional to the visible radiation component passing through said filter element and being independent of the infrared radiation.

11. Light filter means according to claim 9 wherein said subtraction circuit includes a differential amplifier, said first optical sensor being connected to the inverting input thereof and said second optical sensor being connected to the noninverting input thereof so that a positive signal is fed to the regulating circuit, the positive signal being proportional to the visible radiation component passing through said filter element and being independent of the infrared radiation.

12. Light filter means according to claim 1 wherein said first optical sensor and said second optical sensor have the same sensitivity characteristics, and further including an optical band-pass filter arranged in front of said second optical sensor.

13. Light filter means according to claim 1 further including an ultraviolet blocking filter arranged in front of at least one of said first and second optical sensors.

14. Light filter means with automatic regulation of optical transmission comprising:
   first and second liquid crystal filter elements which are adjustable to vary the optical transmission of visible light therethrough;
   a first optical sensor for detecting incident and background light, said first optical sensor producing an electrical signal for regulating the optical transmission of said liquid crystal filter elements in accordance with the radiation received by said first optical sensor, said first optical sensor being arranged behind said first filter element in the radiation emitting direction;
   a second optical sensor being arranged beside or in front of said first filter element in the radiation emitting direction;
   a regulating circuit for controlling the optical transmission of visible light through said liquid crystal filter elements including a subtraction circuit which subtracts the signal generated by one of said first and second optical sensors from the signal of the other of said first and second optical sensors, the output signal of said regulating circuit being at least approximately proportional to the amount of visible light in front of said filter element.

15. Light filter means according to claim 14 wherein said second filter element has a partial area in which the optical transmission does not vary, said first optical sensor being arranged in the radiation emitting direction behind said second filter element and the partial area of said second filter element.

* * * * *